(12) United States Patent
Pal et al.

(10) Patent No.: US 11,967,402 B2
(45) Date of Patent: Apr. 23, 2024

(54) SYSTEM AND METHOD FOR OFFLINE DATA COLLECTION AND SYNCHRONIZATION FOR MANAGING A CLINICAL TRIAL

(71) Applicant: CliniOps Inc., Fremont, CA (US)

(72) Inventors: Avik Kumar Pal, Fremont, CA (US); Yerramalli Subramaniam, Pleasanton, CA (US)

(73) Assignee: CliniOps Inc., Fremont, CA (US)

( * ) Notice: Subject to any disclaimer, the term of this patent is extended or adjusted under 35 U.S.C. 154(b) by 0 days.

(21) Appl. No.: 18/120,064

(22) Filed: Mar. 10, 2023

(65) Prior Publication Data

US 2023/0282317 A1    Sep. 7, 2023

Related U.S. Application Data

(63) Continuation-in-part of application No. 16/857,181, filed on Apr. 24, 2020, now abandoned.

(51) Int. Cl.
*G16H 10/20* (2018.01)
*G16H 10/60* (2018.01)
*G16H 80/00* (2018.01)

(52) U.S. Cl.
CPC .............. *G16H 10/20* (2018.01); *G16H 10/60* (2018.01); *G16H 80/00* (2018.01)

(58) Field of Classification Search
CPC ......... G16H 10/20; G16H 10/60; G16H 80/00
USPC ............................................................ 705/3
See application file for complete search history.

(56) References Cited

U.S. PATENT DOCUMENTS

| 2003/0208378 | A1  | 11/2003 | Thangaraj et al. |
| 2005/0075832 | A1* | 4/2005  | Ikeguchi ............... G16H 70/20 702/179 |
| 2005/0182663 | A1* | 8/2005  | Abraham-Fuchs .... G06Q 30/02 705/3 |

(Continued)

FOREIGN PATENT DOCUMENTS

CN            105389619 B    8/2021

OTHER PUBLICATIONS

Kernan, W. N., Viscoli, C. M., Makuch, R. W., Brass, L. M., & Horwitz, R. I. (1999). Stratified randomization for clinical trials. Journal of clinical epidemiology, 52(1), 19-26. (Year: 1999).*

(Continued)

*Primary Examiner* — Joshua B Blanchette
*Assistant Examiner* — Winston Furtado
(74) *Attorney, Agent, or Firm* — Shumaker, Loop & Kendrick, LLP

(57) ABSTRACT

A system and a method for managing a clinical trial of patients. The method includes obtaining consents of the patients undergoing the clinical trial and storing consent data of the patients. Consent data of the patients is validated before progressing onto any stage of the clinical trial. Data associated with at least one clinical trial site is collected for performing the clinical trial. The patients are randomly grouped into two or more groups for performing one or more of a single blinded study and a double blinded study during the clinical trial. Clinical data and non-clinical data of the patients is collected during the clinical trial. Timelines, progress, compliance, and data associated with different stages of the clinical trial are managed.

19 Claims, 12 Drawing Sheets

(56) References Cited

U.S. PATENT DOCUMENTS

| | | | |
|---|---|---|---|
| 2008/0270181 A1* | 10/2008 | Rosenberg | G16H 10/20 705/7.42 |
| 2011/0166873 A1* | 7/2011 | Griffin | G16H 10/60 705/2 |
| 2011/0313782 A1* | 12/2011 | DeMeyer | G16H 10/20 705/2 |
| 2012/0089418 A1* | 4/2012 | Kamath | G16H 70/40 705/3 |
| 2013/0211805 A1 | 8/2013 | Dwyer | |
| 2015/0039327 A1 | 2/2015 | Pal | |
| 2016/0147963 A1* | 5/2016 | Bouhnik | G16H 40/63 705/2 |
| 2020/0168304 A1* | 5/2020 | Manasco | G16H 10/20 |
| 2021/0335456 A1 | 10/2021 | Pal et al. | |

OTHER PUBLICATIONS

Farrell, B., Kenyon, S., & Shakur, H. (2010). Managing clinical trials. Trials, 11(1), 1-6. (Year: 2010).*

James S. Rao, S.V. & Granger, C.B. (2015). Registry-based randomized clinical trials—a new clinical trial paradigm. Nature Reviews Cardiology, 12(5), 312-316. (Year: 2015).

Rathinavel, K. (2015). Design and Implementation of a Secure Web Platform for a Building Energy Management Open Source Software (Doctoral dissertation, Virginia Tech). (Year: 2016).

* cited by examiner

| Subject ID ⇅ | Site ⇅ | Group ⇅ | Last Updated ⇅ | Logs | | | Registration Visit | Consent Visit | Baseline | | | | | |
|---|---|---|---|---|---|---|---|---|---|---|---|---|---|---|
| | | | | Adverse Event ⇅ | Concomitant medication ⇅ | Demo Date ⇅ | Registration Form ⇅ | Consent Form ⇅ | Demography ⇅ | Diagnosis Intervention and Pathology ⇅ | Vital Signs ⇅ | Inclusion Exclusion ⇅ | Lab ⇅ | Randomization ⇅ |
| PT03230929 | Los Angeles | Treatment 1 | 2023-09-29 18:39:48 | | | | ○ | ○ | ○ | | | ○ | | |
| PT214 | Los Angeles | Treatment 2 | 2023-09-29 17:14:12 | ○ | | | ● | ○ | | | | ○ | | |
| PT191217 | Los Angeles | Treatment 2 | 2023-09-29 14:04:17 | | ○ | | ○ | ○ | | | | ○ | ● | |
| PT0522 | Los Angeles | Treatment 2 | 2023-09-25 06:53:27 | ○ | | ○ | ○ | ○ | | | | ○ | ◉ | |
| PTDIA02 | Los Angeles | Treatment 2 | 2023-09-20 19:04:26 | | | | ✓ | | ✓ | ✓ | ✓ | ✓ | | |

Fig. 3

PT191217 / Baseline / Inclusion Exclusion

Inclusion Criteria

Must have at least 1 measurable lesion per Response Evaluation Criteria in Solid Tumors(RECIST)*  ○ Yes  ○ No Adequate hematopoietic, electrolyte, hepatic, and renal laboratory findings ⓘ *  ○ Yes  ○ No Eastern Cooperative Oncology Group (ECOG) Performance Status ≤1*  ○ Yes  ○ No Exclusion Criteria History of grade 3 or above hypersensitivity reactions to other monoclonal antibodies*  ○ Yes  ○ No Presence of leptomenningeal disease*  ○ Yes  ○ No Subjects with any active, known, or suspected autoimmune disease*  ○ Yes  ○ No Active infection requiring therapy, positive tests for Hepatitis B surface antigen or Hepatitis C ribonucleic acid (RNA) ⓘ *  ○ Yes  ○ No Save Data

- PT03230929
- PT214
- PT191217
  - Logs
  - Registration Visit
  - Consent Visit
  - Baseline
    - Demography
    - Diagnosis Intervention and Pathology
    - Vital Signs
    - Inclusion Exclusion
    - Lab
    - Randomization
    - Study Drug Administration
    - Reproductive status
    - PK Sample
  - Week 1
  - Week 2
  - End of Study
  - Unscheduled ⊕
- PT0522
- PTDIA02
- PT9999

Fig. 4b

| Manage | | | | | | | | | | | | | IRT ▼ |
|---|---|---|---|---|---|---|---|---|---|---|---|---|---|

Treatment Assignment

Randomization
Treatment Assignment

| Copy | CSV | PDF | | | | | | | | | Search: | | |
|---|---|---|---|---|---|---|---|---|---|---|---|---|---|

| Count ⇅ | Subject Id ⇅ | Site ⇅ | Group ⇅ | Arm ⇅ | Epoch ⇅ | Randomization Code ⇅ | Kit Id ⇅ | Randomization Date ⇅ | Assigned By ⇅ | Action ⇅ | Unblinded By ⇅ | Unblinding Date ⇅ |
|---|---|---|---|---|---|---|---|---|---|---|---|---|
| 1 | PT00020727 | Los Angeles | 1-2 | 120 mg | | RZA-1001 | KTX-1001 | 2021-07-27 06:21:03 | Sb1 User | ● | John Smith | 2021-07-30 05:31:28 |
| 2 | PTX00002 | Maputo | 1-2 | ****** | | RZA-1002 | KTX-1002 | 2021-07-27 06:21:35 | Sb1 User | ⊘ | | |

Showing 1 to 2 of 2 entries

Previous 1 Next

Total Records : 16000

Fig. 6

Search Rep

Standard Report

- Adverse Events
- Annotations
- SYS: Data Download
- SYS: Data Upload
- Edit Check Log Report
- Edit Check Summary
- Form Status
- Laboratory Values
- Query Aging
- Query Details Report
- Query Summary
- SAE Report
- SDV Report Adverse Events

[Copy] [CSV] [PDF]

Search:

| Subject ID ↕ | Site ↕ | Adverse Event ↕ | Start Date ↕ | End Date ↕ | Ongoing ↕ | Severity ↕ | Relationship to study ↕ |
|---|---|---|---|---|---|---|---|
| PT214 | Los Angeles | | 09/18/2023 | | 1 | | |
| PT0522 | Los Angeles | | 05/01/2023 | | 1 | | |
| PTX00002 | Maputo | | 06/01/2023 | | 2 | | |
| PTX00002 | Maputo | Chest Pain | 2019-06-24 15:03:09 | 2019-06-24 15:03:09 | N | MILD | POSSIBLY |
| PTX00001 | Maputo | Abdominal Pain | 2019-06-24 15:03:08 | 2019-06-24 15:03:08 | N | MODERATE | POSSIBLY |
| PTX00003 | Maputo | Chest Pain | 2019-06-24 15:03:10 | 2019-06-24 15:03:10 | N | MODERATE | POSSIBLY |
| PTX00004 | Maputo | Chest Pain | 2019-06-24 15:03:11 | 2019-06-24 15:03:11 | N | SEVERE | POSSIBLY |
| PTX00005 | Maputo | Chest Pain | 2019-06-24 15:03:13 | 2019-06-24 15:03:13 | N | MODERATE | POSSIBLY |

Fig. 7

● MedDRA    MedDRA    Search: _____    ○ Auto Code

▫ WhoDRUG    [Copy] [CSV] [PDF]

| Subject ID ↕ | Verbatim ↕ | AELLT ↕ | AELLTCD ↕ | AEDECOD ↕ | AEPTCD ↕ | AEHLT ↕ | AEHLTCD ↕ | AEHLGT ↕ | AEHLGTCD ↕ | AESOC ↕ | AESOCCD ↕ |
|---|---|---|---|---|---|---|---|---|---|---|---|
| 234DFA975 | Myaglia | | | | | | | | | | |
| PTX00001 | Abdominal Pain | Abdominal Pain | 10000081 | Abdominal Pain | 10000081 | Gastrointestinal and abdominal pains (excel oral and throat) | 10017926 | Gastrointestinal signs and symptoms | 10018012 | Gastrointestinal disorders | 10017947 |
| PTX00002 | Chest Pain | Chest Pain | 10008479 | Chest Pain | 10008479 | Ischaemic coronary artery disorders | 10011085 | Coronary artery disorders | 10011082 | General disorders and administration site conditions | 10018065 |
| PTX00003 | Chest Pain | Chest Pain | 10008479 | Chest Pain | 10008479 | Ischaemic coronary artery disorders | 10011085 | Coronary artery disorders | 10011082 | General disorders and administration site conditions | 10018065 |
| PTX00004 | Chest Pain | Chest Pain | 10008479 | Chest Pain | 10008479 | Ischaemic coronary artery disorders | 10011085 | Coronary artery disorders | 10011082 | General disorders and administration site conditions | 10018065 |
| PTX00005 | Chest Pain | Chest Pain | 10008479 | Chest Pain | 10008479 | Ischaemic coronary artery disorders | 10011085 | Coronary artery disorders | 10011082 | General disorders and administration site conditions | 10018065 |
| PTX00006 | Chest Pain | Chest Pain | 10008479 | Chest Pain | 10008479 | Ischaemic coronary artery disorders | 10011085 | Coronary artery disorders | 10011082 | General disorders and administration site conditions | 10018065 |

Fig. 9

SYSTEM AND METHOD FOR OFFLINE DATA COLLECTION AND SYNCHRONIZATION FOR MANAGING A CLINICAL TRIAL

CROSS-REFERENCE TO RELATED APPLICATIONS AND PRIORITY

The present U.S. Utility Patent Application is a continuation in part of U.S. Utility application Ser. No. 16/857,181, entitled "Systems and methods for collecting clinical and non-clinical data across multiple functional modules through a central gateway", filed Apr. 24, 2020.

TECHNICAL FIELD

The present subject matter described herein, in general, relates to the field of clinical trial management, and more particularly to establishment of a cloud network for managing a clinical trial.

BACKGROUND

A clinical trial is a research study performed on patients for evaluating effect of a medical procedure or a drug on the patients. A clinical trial involves different phases that include different numbers of patients. Generally, patients of different ages, sexes, races, and ethnicities are required to participate in a clinical trial so that an outcome of the clinical trial has wider applicability.

Conducting a successful clinical trial is a complex process due to the collaborative nature, multiple stakeholders, multi variate data sources and the high stakes involved in running a clinical trial. Conventionally, different types of activities are associated with a clinical trial and different types of data associated with each activity.

A wide range of coordination is also needed that involves the sites (hospitals or health centres), the subjects (patients or participants), the principal investigators (physicians or researchers), the site coordinators (nurses or care givers), the sponsors (the pharma, biotech or medical device company that is sponsoring the clinical trial), the clinical research organizations (CRO) who are providing the services to run these large multi-country global clinical trial, the biostatisticians who analyze the data collected during the trial and the regulatory bodies or agencies such as Food and Drug Administration (FDA), European Medicines Agency (EMA) and similar agencies worldwide who review the final data submitted for a go/no-go decision or approval of the drug to market.

There is a need of a system and method that can be used to effectively manage a clinical trial for patients and eliminates the different challenges associated with the existing approaches.

SUMMARY

Before the present systems and methods for managing a clinical trial of patients are described, it is to be understood that this application is not limited to the particular systems, and methodologies described, as there can be multiple possible embodiments which are not expressly illustrated in the present disclosures. It is also to be understood that the terminology used in the description is for the purpose of describing the particular implementations or versions or embodiments only, and is not intended to limit the scope of the present application.

This summary is provided to introduce aspects related to a system and a method for managing a clinical trial of patients. This summary is not intended to identify essential features of the claimed subject matter nor is it intended for use in determining or limiting the scope of the claimed subject matter.

In one implementation, a system for managing a clinical trial of patients is disclosed. In one aspect, the system comprises a processor and a memory coupled to the processor. The memory stores programmed instructions executable by the processor. Specifically, the processor implements a consent recorder for obtaining consent of the patients undergoing the clinical trial and storing consent data of the patients. The clinical trial comprises a study setup stage, a study conduct stage, and a study closeout stage. The processor further implements a consent validator for validating consent data of the patients before progressing onto the study setup stage, the study conduct stage, and the study closeout stage of the clinical trial. The processor further implements a clinical site data collector for collecting data associated with at least one clinical trial site for performing the clinical trial. The processor further implements a randomizer for randomly grouping the patients into two or more groups for performing one or more of a single blinded study and a double blinded study during the clinical trial. The processor further implements a patient data collector for collecting clinical data and non-clinical data of the patients during the clinical trial. The clinical data includes medical details of the patients collected before and after administration of a drug during the clinical trial and the non-clinical data includes personal details and documents of the patients collected for performing patient registration and administration for the clinical trial. The processor further implements a centralized trial manager for managing one or more of timelines, progress, compliance, and data associated with different stages of the clinical trial.

In one aspect, the patient data collector allows a real time interaction between the patients and the clinical trial site and provides automated notifications to the patients and the clinical trial site for recording one or more of the clinical data and the non-clinical data associated with the clinical trial, based on the timelines.

In one aspect, a data visualizer provides a combined analysis of the data associated with the clinical trial site, the clinical data, and the non-clinical data of the patients in real time.

In one aspect, the centralized trial manager is integrated with the clinical site data collector for mapping one or more adverse events reported by the patients and one or more adverse events identified at the clinical trial site.

In one aspect, the system is connected with a user device including an offline data recorder capable of recording the clinical data when the user device lacks internet access. The user device includes a communication unit for communicating the clinical data to the system when the user device has internet access.

In one aspect, the randomizer randomly groups the patients into two or more groups based on the clinical data and the non-clinical data collected by the patient data collector.

In one aspect, the randomizer assigns a unique Quick Response (QR) code to each of the patients, for allowing the patients to track and complete activities associated with one or more of the single blinded study and the double blinded study.

In one aspect, a clinical trial auditor provides an audit trail report and allowing a real time inspection of studies performed during the clinical trial. The audit trail report includes details of when and who added or modified data captured during the clinical trial.

In one aspect, the clinical trial auditor is integrated with the clinical site data collector for automatically fetching details of a new clinical trial site defined in the clinical site data collector.

In one aspect, the consent recorder provides access to one or more of:
compliance data of the clinical trial sites;
consent data of the patients, tagged with a time stamp and a geographic location; and
Patients' Health Information (PHI), wherein a partial access or a complete access of the PHI is provided to a user based on access rights defined for the user.

In one aspect, the clinical site data collector is connected with one or more Electronic Health Records (EHRs) for automatically retrieving a digital information of the patients from the one or more EHRs.

In one aspect, the randomizer randomly groups the patients by obtaining details from the clinical site data collector for performing the blinded study.

In one aspect, an automatic medical coder generates a mapping of medical terms with standard dictionary terms.

In one implementation, a method for managing a clinical trial of patients is disclosed. The method may comprise obtaining consents of the patients undergoing the clinical trial and storing consent data of the patients. The clinical trial comprises a study setup stage, a study conduct stage, and a study closeout stage. The method may further comprise validating consent data of the patients before progressing onto the study setup stage, the study conduct stage, and the study closeout stage of the clinical trial. The method may further comprise collecting data associated with at least one clinical trial site for performing the clinical trial. The method may further comprise randomly grouping the patients into two or more groups for performing one or more of a single blinded study and a double blinded study during the clinical trial. The method may further comprise collecting clinical data and non-clinical data of the patients during the clinical trial. The clinical data includes medical details of the patients collected before and after administration of a drug during the clinical trial and the non-clinical data includes personal details and documents of the patients collected for performing patient registration and administration for the clinical trial. The method may further comprise managing one or more of timelines, progress, compliance, and data associated with different stages of the clinical trial.

BRIEF DESCRIPTION OF THE DRAWINGS

The foregoing detailed description of embodiments is better understood when read in conjunction with the appended drawings. For the purpose of illustrating of the present subject matter, an example of construction of the present subject matter is provided as figures; however, the invention is not limited to the specific method and system disclosed in the document and the figures.

The present subject matter is described in detail with reference to the accompanying figures. In the figures, the left-most digit(s) of a reference number identifies the figure in which the reference number first appears. The same numbers are used throughout the drawings to refer various features of the present subject matter.

FIG. 3 illustrates an exemplary User Interface (UI) of a Case Report Form (CRF) developed using details collected by a clinical site data collector, in accordance with an embodiment of the present subject matter.

FIGS. 4a and 4b illustrate exemplary UIs for collection of data by a patient data collector, in accordance with an embodiment of the present subject matter.

FIG. 6 illustrates a UI showing details of patients grouped randomly into different groups by a randomizer, in accordance with an embodiment of the present subject matter.

FIG. 7 illustrates a UI showing details of adverse events provided by a centralized trial manager, in accordance with an embodiment of the present subject matter.

FIG. 9 illustrates a UI showing coded terms generated by an automatic medical coder using MedDRA library, in accordance with an embodiment of the present subject matter.

DETAILED DESCRIPTION

Figure 1:
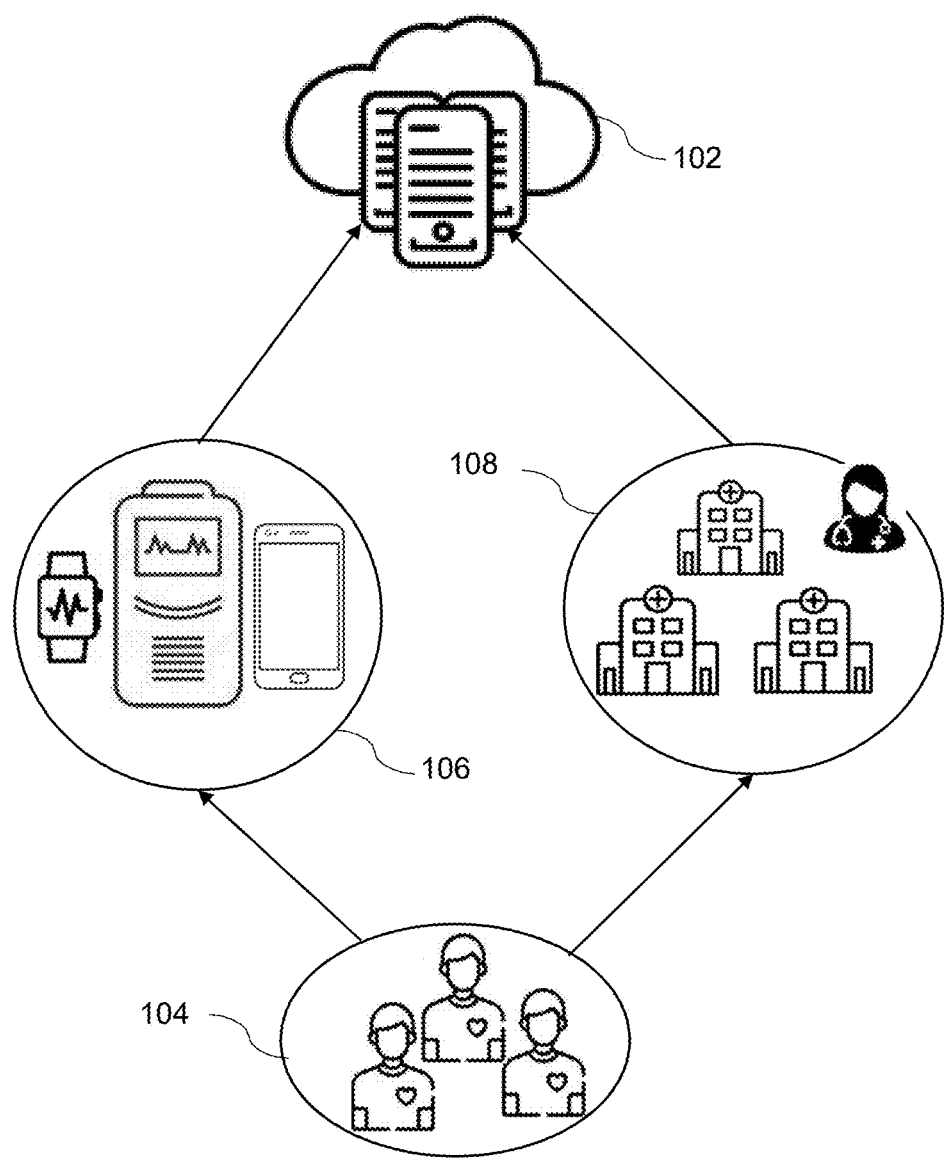
FIG. 1 illustrates a schematic diagram for managing a clinical trial of patients, in accordance with an embodiment of the present subject matter.

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Although any system and method for managing a clinical trial of patients, similar or equivalent to those described herein can be used in the practice or testing of embodiments of the present disclosure, the exemplary, methods and systems for managing a clinical trial of patients are now described. The disclosed embodiments for managing a clinical trial of patients are merely examples of the disclosure, which may be embodied in various forms.

Various modifications to the embodiment will be readily apparent to those skilled in the art and the generic principles herein may be applied to other embodiments for managing a clinical trial of patients. However, one of ordinary skill in the art will readily recognize that the present disclosure for managing a clinical trial of patients is not intended to be limited to the embodiments described, but is to be accorded the widest scope consistent with the principles and features described herein.

Certain technical challenges exist in managing clinical trial data using conventional methods. In the conventional methods, different types of data are collected by the different systems during a clinical trial and different systems are required to be integrated. Integration of the different systems and enabling data exchange between them adds a lot of complexity to the clinical trial which in itself is a complex process. Further, integration of the different systems also affects quality of the data and leads to several errors in the clinical trial.

Additionally, to evaluate progress of the clinical trial and make clinical decisions, concerned individuals responsible for managing the clinical trial are required to individually access the different systems. In this manner, the concerned individuals are not able to obtain view the details in a holistic manner and in a chronological order i.e. in a sequence of occurrence of different activities during the clinical trial.

Many times, a doctor is required to collect patient data in an offline environment i.e. in absence of internet connectivity. Such situations may arise due to presence of dead corners that are beyond the reach of network devices in a clinical trial site or due to complete absence of internet in the clinical trial site due to compliance requirements of the clinical trial. During such situation, the patient data collected by the doctor remains stored in a memory of the user device operated by the doctor and is not made available to a central database configured to store all the patient data.

Furthermore, sometimes the patient data is made available in form of physical documents, and scanned copies or images of such physical documents also do not reach the central database. Due to such reasons, complete information is not utilized during the clinical trial and this adversely affects the outcome of the clinical trial. The present disclosure provides technical solution to the problems in conventional approach of managing the clinical trial data.

Referring now to FIG. 1 illustrating a schematic diagram for managing a clinical trial of patients, in accordance with an embodiment of the present subject matter. As illustrated, a system 102 may collect data of patients 104 participating in the clinical trial. The system 102 may be a device having enormous processing and data storage capability, and can be implemented locally or remotely at a network cloud.

The data of the patients 104 may be collected through electronic devices 106 accessed by the patients 104 or clinical trial sites 108 visited by the patients 104. In some implementations, the electronic devices 106 may include, but not limited to, smart wearable devices, portable medical observation devices, and smartphones. The patients 104 may provide their clinical data and non-clinical data through the electronic devices 106. For example, the patients 104 may provide their personal information and associated documents i.e. one of the non-clinical data using a software application installed on their smartphones while participating in the clinical trial.

Further, the patients 104 may provide their medical details and associated documents i.e. one of the clinical data through the smart wearables like a smart watch worn by them. It may be understood that the clinical data and the non-clinical data may be present in several data formats including an alphanumeric code, an image, a voice note, a video recording, and a wave format. The patients 104 may visit one or more of the clinical trial sites 108, during different stages of the clinical trial, for inoculation of drug and subsequent follow-ups.

Alternatively, the patient 104 may provide the clinical data and the nonclinical data from home by himself. In one other example, the patient 104 may invite a nurse or a doctor at home to collect the clinical data and the non-clinical data. In yet another example, the patient 104 may consult the doctor telephonically to provide the clinical data and the non-clinical data through telephone while the clinical data and the non-clinical data is entered by the doctor into the system 102. The clinical data and the nonclinical data of the patients 104 may be collected by the clinical trial sites 108 during all the stages of the clinical trial.

The clinical data and the non-clinical data of the patients 104 collected by the electronic devices 106 and/or the clinical trial sites 108 may be provided to the system 102. Apart from the data of the patients 104, the system 102 may collect other data, such as data associated with the clinical trial sites 108 and different functions performed during the clinical trial at the clinical trial site. Elaborative details of such functions and different types of the other data have been provided successively with reference to FIG. 2.

Figure 2:
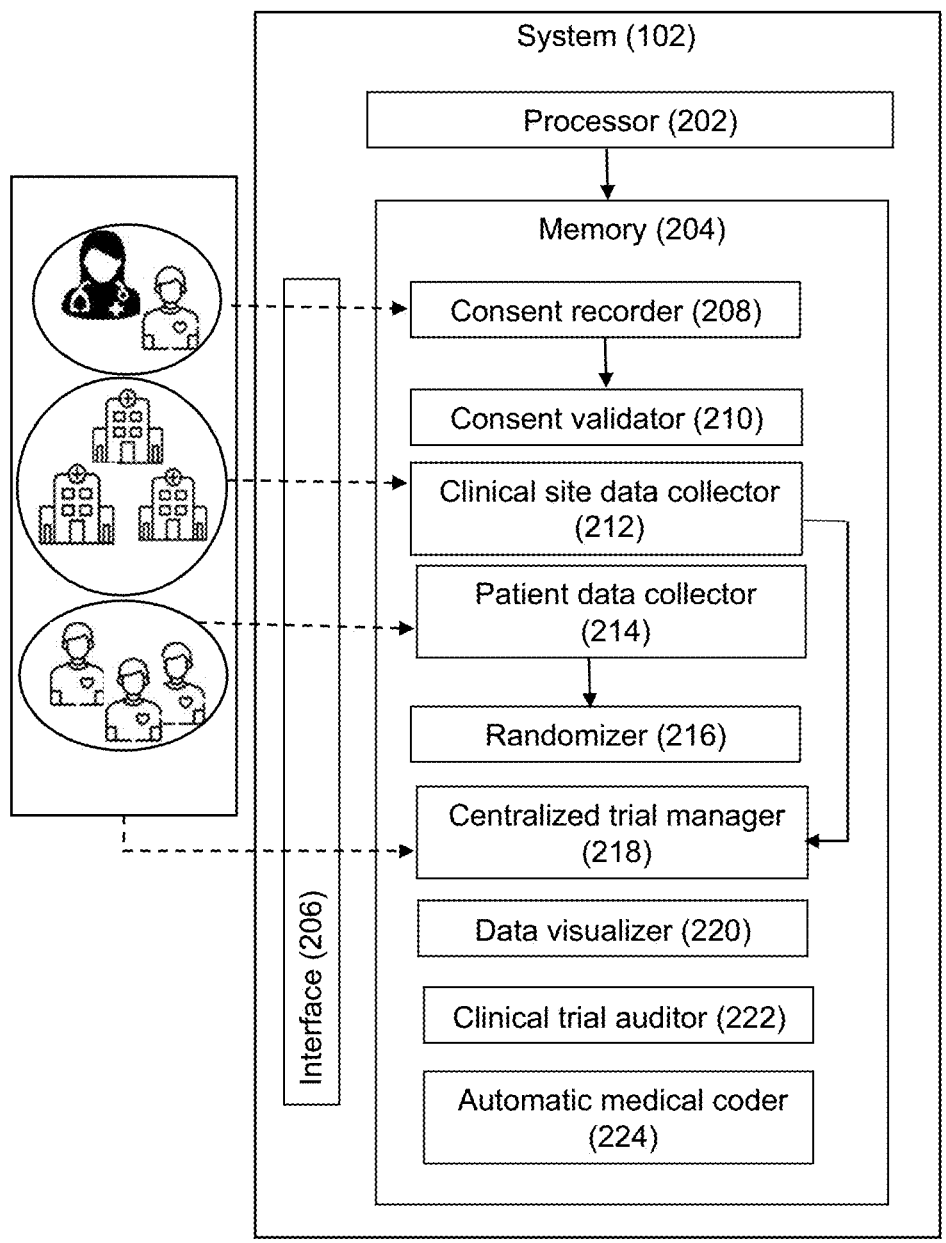
FIG. 2 illustrates a block diagram of the system for managing the clinical trial, in accordance with an embodiment of the present subject matter.

FIG. 2 illustrates a block diagram of the system 102 for managing the clinical trial, in accordance with an embodiment of the present subject matter. In one embodiment, the system 102 may include a processor 202, a memory 204, and an interface 206. The processor 202 and the memory 204 may be accessed through the interface 206. The processor 202 may be implemented as one or more microprocessors, microcomputers, microcontrollers, digital signal processors, central processing units, state machines, logic circuitries, and/or any devices that manipulate signals based on operational instructions. Among other capabilities, the processor 202 may be configured to fetch and execute computer-readable instructions stored in the memory 204.

The memory 204, amongst other things, serves as a repository for storing data processed, received, and generated by the system 102. The memory 204 may include any computer-readable medium including, for example, volatile memory, such as Static Random Access Memory (SRAM) and Dynamic Random Access Memory (DRAM), and/or non-volatile memory, such as Read Only Memory (ROM), Erasable Programmable ROM (EPROM), Electrically Erasable and Programmable ROM (EEPROM), flash memories, hard disks, optical disks, and magnetic tapes.

The system 102 implements a consent recorder 208. The consent recorder 208 may obtain consents of the patients 104 registered for the clinical trial. The consent recorder 208 guides the patients 104 about risks and benefits of the clinical trials, and hence enables the patients 104 to take informed decisions of enrolment for the clinical trial. The consent recorder 208 allows the patients 104 to provide their consents in-person at a clinical trial site, remotely over tele-visit sessions, and through the user device. The consents could be obtained from the patients 104 themselves, their Legally Authorized Representatives (LARs), and family members of the patients 104. It may be understood that each clinical trial site would be connected to a defined number of patients and several such clinical trial sites in same or different cities may participate in the clinical trial.

The consent recorder 208 is also capable of recording a session of guiding a patient and obtaining his consent. The consent data may comprise but not be limited to a consent form signed by the patient, wherein the patient provides consent to undergo and participate in the clinical trial with own desire. Further, obtaining the consent data ensures that the patient understands risks associated with the clinical trial and accepts proceeding despite the risks. Furthermore, the consent data may also comprise a date on which the patient signed the consent form. The consent recorder 208 may also capture time stamps and geo-locations of the patients 104 while obtaining their consents.

Further, the consent recorder 208 provides access to one or more of compliance data of the clinical trial sites, consent data of the patients 104 tagged with a time stamp and a geographic location, and Patients' Health Information (PHI). A partial access or a complete access of the PHI is provided to a user based on access rights defined for the user. Further, the compliance data of the clinical trial sites may be understood to be associated with adherence of the clinical trial sites with a medical standard set by Clinical Data Interchange Standards Consortium (C-DISC) or similar standards set for the clinical trial data.

The system 102 further implements a consent validator 210 for determining whether the consents are obtained from all the patients 104. In one embodiment the consent validator 210 may also determine if the consent is obtained authentically from the patients or falsely by an imposter, a medical professional, a nurse or any person at the clinical trial site for compliance purposes only. In order to do so the consent validator may share a unique authentication code with the user device and request the patient to enter the authentication code. For patients whose consents are not available in the consent recorder 208, the consent validator 210 may trigger alerts. Such alerts would prompt the patients 104 to provide their consents before undergoing any stage of the clinical trial.

The system 102 further implements a clinical site data collector 212. The clinical site data collector 212 is connected with one or more Electronic Health Records (EHRs) for automatically retrieving a digital information of the patients 104 from the one or more EHRs.

FIG. 3 illustrates an exemplary User Interface (UI) of a Case Report Form (CRF) developed using details collected by the clinical site data collector 212, in accordance with an embodiment of the present subject matter. Within the CRF, each row corresponds to a patient, along with a clinical site, treatment group, and date and time stamp of last update of the patient. The CRF also shows status of different forms that the patient has completed. The status of the forms is depicted through icons associated with each form. The status of the forms may be one of unfilled, partially filled, fully filled, filled with errors, reviewed, locked, and a Principal Investigator (PI) sign-off. The PI sign-off status may be understood as a final status of the form wherein the form is reviewed and signed by an authorized signatory such as the PI.

The icon of any form could be clicked for opening the form for review, follow-up action, or next steps as needed. In one example the icon may be a graphical icon displayed on an user interface on the user device. Once the forms are in a locked state, the PI sign-off is initiated. Upon completion of the clinical trial, data can be exported in various formats as appropriate for analysis and long term archival such as a comma-separated values (CSV) format, an Extensible Markup Language (XML) format, an export file format like XPT, and a Portable Document Format (PDF) format.

The system 102 further implements a patient data collector 214 to collect clinical data and non-clinical data of the patients also together referred as patient data. The patient data may be understood as clinical data and non-clinical data associates of the patient. The patient data collector 214 may allow a real time interaction between the patients 104 and the clinical trial site and provide automated notifications to the patients 104 and the clinical trial site for recording one or more of the clinical data and the non-clinical data associated with the clinical trial, based on the timelines in a compliance calendar. In one example, the compliance calendar may be created specifically for the clinical trial mentioning date, time, and a type of clinical data and non-clinical data (such as a body temperature, a blood pressure) to be provided at each stage of the clinical trial. It may be understood that the compliance calendar may not be editable and can be provided digitally to the patients, the clinical trial sites, the hospitals, the doctors and the nurses.

Further, any non-compliance in the compliance calendar may lead to generation of an alert or a reminder by the system 102 on the user device of the patients and the clinical trial sites. It may be noted that the non-compliance of the compliance calendar appears in the audit trail reports for the clinical trial site. Furthermore, multiple alerts or reminders for the non-compliance of the compliance calendar may indicate an efficiency of the clinical trial site during a time duration for the clinical trial.

In one example, a sponsor of the clinical trial may utilize the compliance calendar as a measure to track the efficiency and a performance of the clinical trial site with respect to one or more other clinical trial sites participating in the clinical trial. It may be understood that timely obtaining the clinical data and the non-clinical data of the patients registered at the clinical trial site is a responsibility of the patients as well as the clinical trial sites. Therefore, the clinical trial site may take advanced measures to configure the system 102 to ensure optimal compliance as per the compliance calendar by all the patients registered at the clinical trial site.

The patient data collector 214 may also collect details of medical history and current health status of patients 104 and data of medical check-ups performed during the clinical trial. The tests may include but not be limited to blood tests, urine tests, genetic tests, X-ray scans, Computerized Tomography (CT) scans, and Magnetic Resonance Image (MRI) scans. Results of such medical check-ups may be used to determine efficacy of a drug or a vaccine required to be tested during the clinical trial.

Figure 4A:
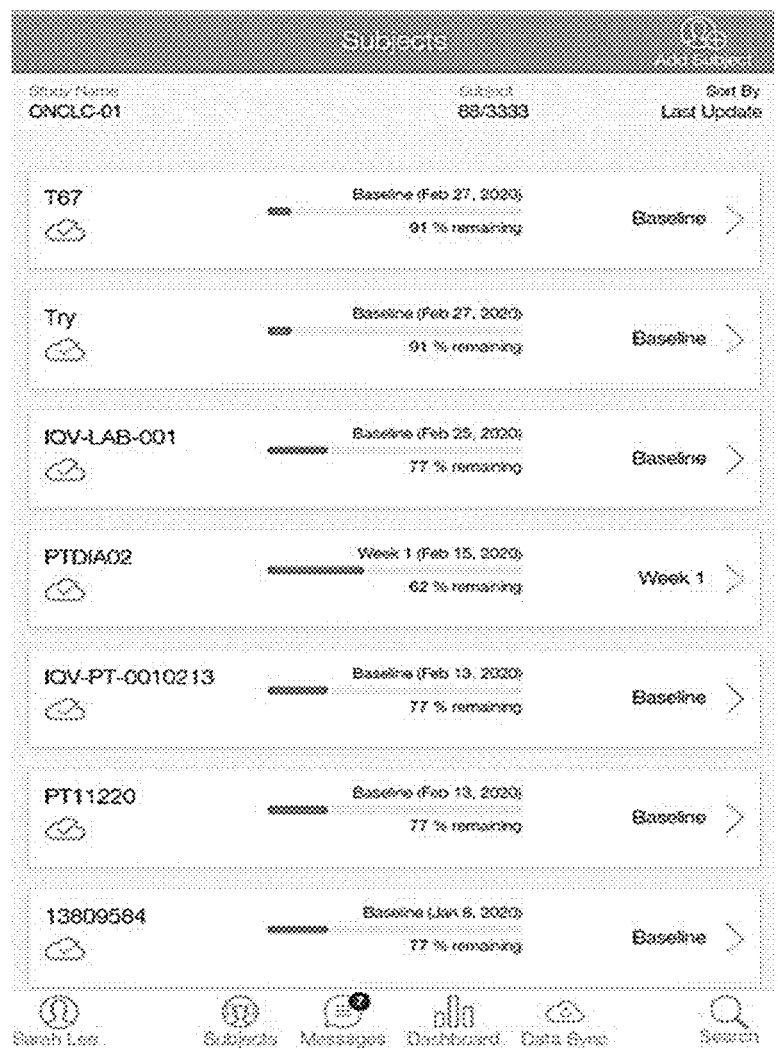

FIGS. 4a and 4b illustrate exemplary UIs for collection of data by the patient data collector 214, in accordance with an embodiment of the present subject matter. As illustrated in FIG. 4a, the patient data collector 214 may collect patient data across different visits of the clinical sites. Once a patient ID is selected on the UI, the compliance calendar particular to the patient for the clinical trial is shown. The compliance calendar may include a plan of all the visits associated with that patient and dates of the visits. It may be understood that the patient may choose to provide the clinical data and the non-clinical data from the patient's home and the hospital on the dates mentioned in the compliance calendar.

Each visit represents the forms tied to that visit, and each form has all the data fields required to be collected during that visit. As illustrated in FIG. 4b, unique identities of each patient, status of their next visit at a clinical trial site, and status date could be shown by the patient data collector 214.

A doctor is constantly required to visit the patients 104 in a clinical trial site and collect clinical data and non-clinical data of the patients 104 on the user device. In some scenarios, there are restrictions on usage of internet or network is unavailable in certain areas of the clinical trial site. Therefore, the doctor may need to collect the clinical data without internet connectivity in such scenarios. To ensure seamless collection of the clinical data and the non-clinical data on the user device, an offline data collection feature is provided. Such feature enables the doctor to collect clinical data of the patients 104 on the user device even in absence of internet connectivity.

Figure 5:
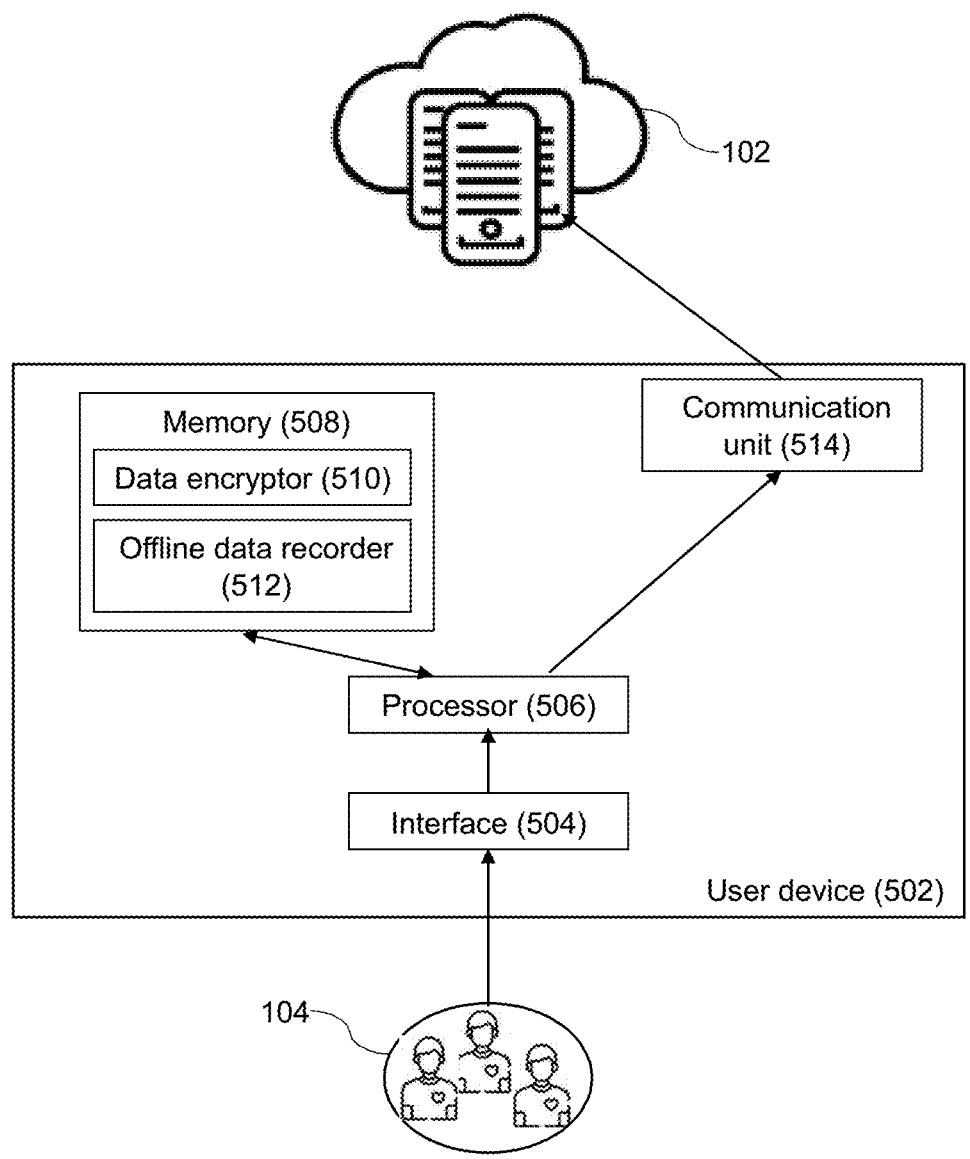
FIG. 5 illustrates a block diagram of a user device configured to collect and transfer clinical data of patients to the system, in accordance with an embodiment of the present subject matter.

FIG. 5 illustrates a block diagram of a user device 502 configured to collect and transfer the clinical data of patients 104 to the system 102, in accordance with an embodiment of the present subject matter. The user device 502 may include an interface 504, a processor 506, and a memory 508. By accessing the interface 504 of the user device 502, a doctor may feed clinical data of the patients 104. The processor 506 may forward the clinical data to the memory 508. The memory 508 may include a data encryptor 510 and an offline data recorder 512.

The data encryptor 510 may encrypt the clinical data using a suitable data encryption scheme, such as Advanced Encryption Standard (AES), Triple Data Encryption Standard (TDES), Rivest Shamir Adleman (RSA), Blowfish, Twofish, Format-Preserving Encryption (FPE), and Elliptic Curve Cryptography (ECC). The memory 508 may include an offline data recorder 512 for storing the patient data encrypted by the data encryptor 510.

The offline data recorder 512 may store the patient data till completion of the clinical trial and archive the patient data post completion of the clinical trial for reference purposes. When the user device 502 gains internet connectivity, a communication unit 514 present in the user device 502 may wirelessly communicate the patient data collected offline without internet connectivity to the system 102. The patient data may be communicated to the system 102 automatically or based on the doctor's instruction. The offline data recorder 512 may assign a time stamp and a geographical location to the patient data collected even while offline i.e. without any internet connectivity. Further, the system 102 may record and reflect the time stamp and the geographical location in the user device. It may be understood that the time stamp and the geographical location during offline collection of the patient data is non-editable.

The system 102 further implements a randomizer 216 for randomly grouping the patients 104 into two or more groups, for performing a single blinded study and/or a double blinded study during the clinical trial. The single blinded study may be understood to provide visibility of a test only to a doctor and not to a patient undergoing the test. Whereas, the double blinded study may be understood to not provide visibility of the test to both the doctor and the patient. The randomizer 216 randomly groups the patients 104 into the two or more groups based on the clinical data and the non-clinical data collected by the patient data collector 214.

Further, the randomizer 216 may also randomly group the patients 104 by obtaining details from the clinical site data collector 212 for performing the blinded study. The randomizer 216 assigns a unique QR code to each of the patients 104, for allowing the patients 104 to track and complete activities associated with one or more of the single blinded study and the double blinded study. The randomizer 216 randomly groups the patients 104 based on the clinical data and the non-clinical data collected by the patient data collector 214 instead of data provided manually by the patients 104. Therefore the output of the randomizer 216 is error free.

FIG. 6 illustrates a UI showing details of patients 104 grouped randomly into different groups also referred to as different treatment arms by the randomizer 216, in accordance with an embodiment of the present subject matter. The randomizer 216 provides support for both simple and advanced randomization algorithms based on a permuted blocked stratification and a minimization technique for randomization. The randomizer 216 also provides the capability for tracking medical kits and emergency unblinding of patient details. The randomizer 216 can generate standardized reports usable for tracking progress of the patients 104 within the clinical trial in real-time.

The system 102 further implements a centralized trial manager 218 responsible for managing timelines, progress, compliance, and data associated with different stages of the clinical trial based on the compliance calendar. The centralized trial manager 218 is integrated with the clinical site data collector 212 for mapping one or more adverse events reported by the patients 104 and one or more adverse events identified at the clinical trial site. The adverse event may be understood as any unexpected medical event occurring during the clinical trial. The centralized trial manager 218 provides a summarized information of the adverse events reported at each of the clinical trial sites, without any need for custom integration.

FIG. 7 illustrates a UI showing details of the adverse events provided by the centralized trial manager 218, in accordance with an embodiment of the present subject matter. For example, for a patient having a subject ID: PTX00001, an adverse event of 'abdominal pain' was reported at a clinical trial site Maputo. It may be understood that every patient participating in the clinical trial may be provided a subject ID to mask the identity of the patient. The adverse event was reported to be of moderate severity and having a possible link to the clinical trial.

Further, the centralized trial manager 218 collects detail available with the consent recorder 208, the clinical site data collector 212, and the patient data collector 214, and may hold such detail centrally. The centralized trial manager 218 may collect such detail from the patients 104 and the clinical trial sites or may obtain a copy of the details available with the consent recorder 208, the clinical site data collector 212, and the patient data collector 214.

The system 102 further implements a data visualizer 220 allowing generation and visualization of different analysis reports associated with the clinical trial. The data visualizer 220 provides a combined analysis report based on one or more parameters of the data associated with the clinical trial site, the clinical data, and the non-clinical data of the patients 104 in real time. In one example, the data visualizer 220 may provide the combined analysis report with respect to a change in pain level for all patients registered at the clinical trial site over time of the clinical trial.

In one other example, the data visualizer 220 may provide the combined analysis report for a compliance level achieved by each of the clinical trial site participating in the clinical trial, indicating the most compliant clinical trial site during a given time duration. In one other example, the data visualizer 220 may provide a number of patients dropping out of the clinical trial over time to indicate a rate of dropouts of the patients 104.

In one other example, the data visualizer 220 may provide insights on most serious symptoms observed among the patients 104 of the clinical trial site undergoing the clinical trial. The most serious symptoms may be associated with the drug being administered to the patient 104 and may be one or more of nausea, headache, allergic reactions, diarrhea and the like.

In one example if the clinical trial comprises a single blinded study or a double blinded study, the combined analysis report may provide insights on the progression of the respective single blinded study or the double blinded study vis-à-vis the patients at the clinical trial site. Therefore, the combined analysis report may be generated using one or more parameters measured or obtained using the clinical data and the non-clinical data of the patients.

Figure 8:
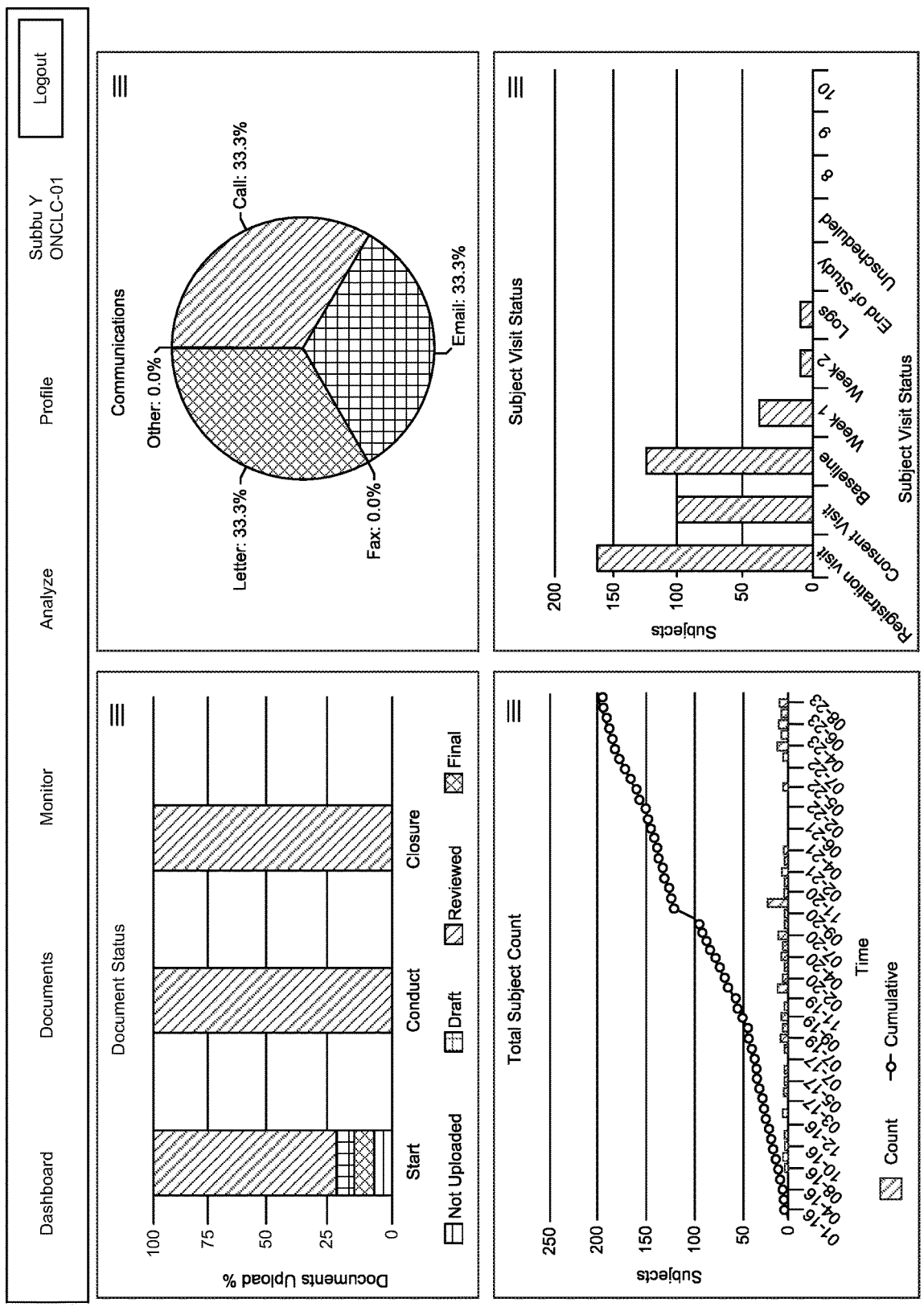
FIG. 8 illustrates a UI showing different reports generated using a data visualizer, in accordance with an embodiment of the present subject matter.

FIG. 8 illustrates a UI showing different reports generated using the data visualizer 220, in accordance with an embodiment of the present subject matter. As illustrated, the reports may provide status of documents of the patients 104, mode of communication with the patients 104 and doctors, total count of patients 104, and status of visit of the patients 104. In FIG. 8 patients are referred to as subjects.

The system 102 further implements a clinical trial auditor 222 for providing an audit trail report and allowing a real time inspection of studies performed during the clinical trial. The audit trail report includes identity details of the patients 104 and the doctors who added or modified any data during the clinical trial and the timestamps related to addition or modification of the data. The clinical trial auditor 222 is integrated with the clinical site data collector 212 for automatically fetching details of a new clinical trial site defined in the clinical site data collector 212. The new clinical trial site may be understood as a clinical trial site required to be newly registered for performing the clinical trial.

The system 102 further implements an automatic medical coder 224. The automatic medical coder 224 codes data collected during the clinical trial against standard coding libraries, such as Medical Dictionary for Regulatory Activities (MedDRA) and World Health Organization dictionary (WHODrug), and displays coded terms. In other words, the automatic medical coder 224 generates a mapping of medical terms with dictionary terms as per the standard coding libraries MedDRA and WHODrug.

FIG. 9 illustrates a UI showing coded terms generated by the automatic medical coder 224 using the MedDRA library, in accordance with an embodiment of the present subject matter. As illustrated in FIG. 9, in one case, for a patient having subject ID 'PTX00001', the patient data collector 214 received a verbatim adverse event term 'Abdominal Pain' from a clinical trial site. The automatic medical coder 224 mapped this verbatim adverse event term with corresponding entries present in the MedDRA dictionary or a similar medical dictionary.

Data collected by the consent recorder 208, the consent validator 210, the clinical site data collector 212, the patient data collector 214, the randomizer 216, the centralized trial manager 218, the data visualizer 220, and the clinical trial auditor 222 is stored in a linked manner using foreign key relations.

Figure 10:
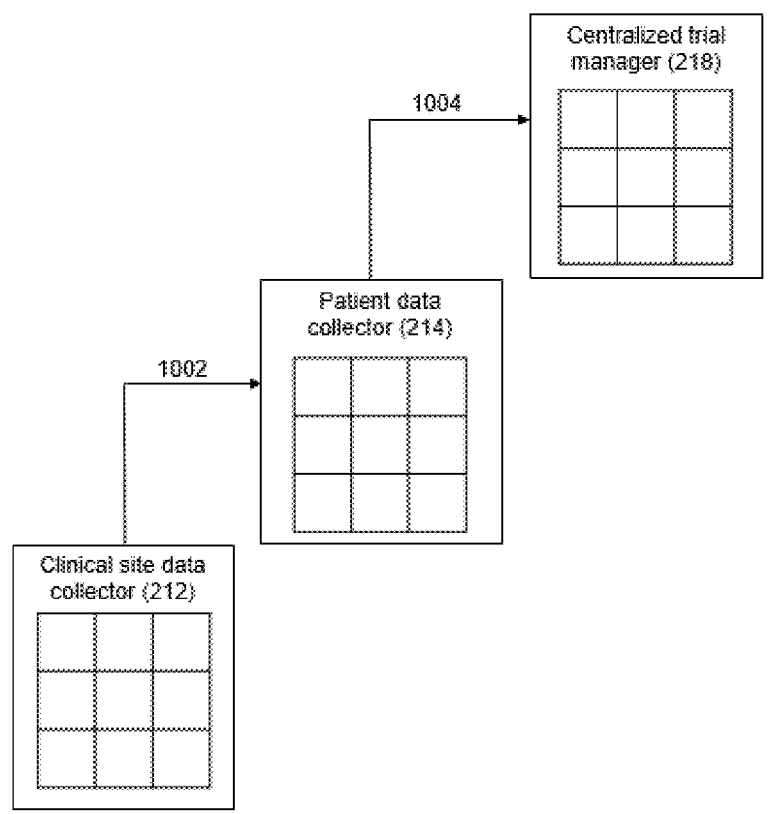
FIG. 10 illustrates a linked relationship between different data files developed by the system, in accordance with an embodiment of the present subject matter.

FIG. 10 illustrates a linked relationship between different data files developed by the system 102, in accordance with an embodiment of the present subject matter. Specifically, the different data files may be developed by the clinical site data collector 212, the patient data collector 214, and the centralized trial manager 218. At least one foreign key link 1002 may be present between the data file of the clinical site data collector 212 and the data file of the patient data collector 214.

Further, at least one foreign key link 1004 may be present between the data file of the patient data collector 214 and the data file of the centralized trial manager 218. In this manner, all the data files developed by the system 102 may function as a single source of data. Such single source of data would prevent the need of providing same data by the patients 104 at different stages of the clinical trial. The single source of data would also prevent entering of wrong information by patients 104 which would result into inaccurate observations being derived from the clinical trial.

Further, with presence of such single source of data with the centralized trial manager 218, it becomes possible to view all the details in a holistic manner and in a chronological order i.e. in a sequence of occurrence of different activities during the different stages of the clinical trial.

To collect more data for performing the clinical trial, the system 102 can connect with Electronic Health Records (EHRs) available with third parties, patient data recorders managed by third parties, and any other module storing data relevant for performing the clinical trial.

Upon completion of all the stages of a clinical trial, the data collected and/or generated by one or more of the consent recorder 208, the consent validator 210, the clinical site data collector 212, the patient data collector 214, the randomizer 216, the centralized trial manager 218, the data visualizer 220, and the clinical trial auditor 222 is used for determining compliance of each stage of the clinical trial with set medical standards and determining efficacy of the drug or the vaccine required to be tested during the clinical trial.

Figure 11:
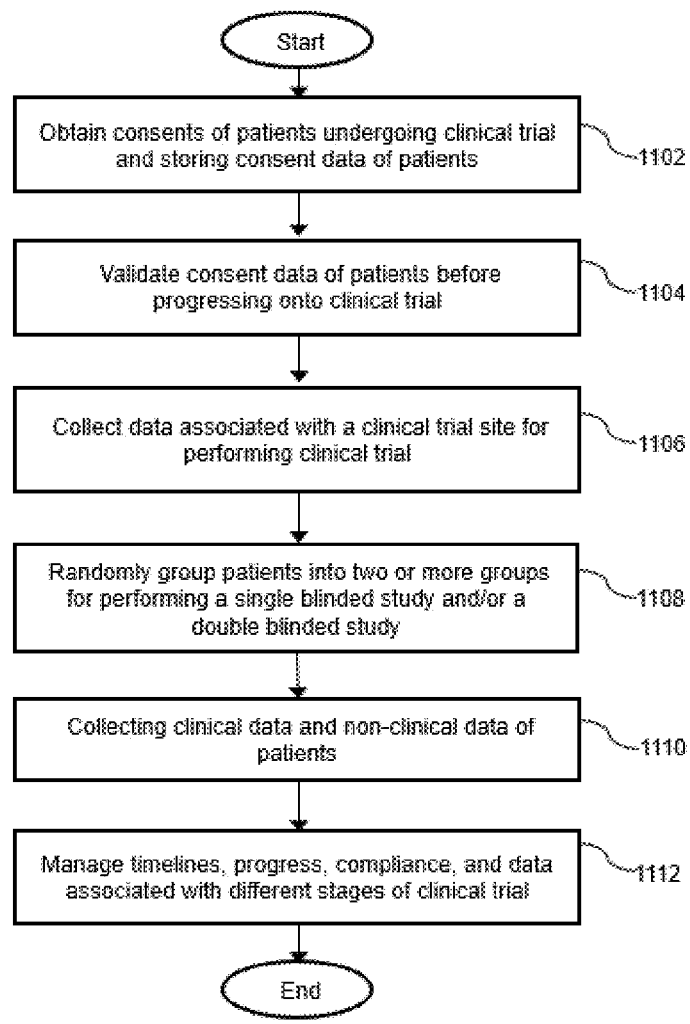
FIG. 11 illustrates a flow chart of a method for managing a clinical trial of patients, in accordance with an embodiment of the present subject matter.

FIG. 11 illustrates a flow chart of a method for managing a clinical trial of patients 104, in accordance with an embodiment of the present subject matter. The order in which the method for managing a clinical trial of patients 104 is described is not intended to be construed as a limitation, and any number of the described method blocks can be combined in any order to implement the method or alternate methods.

Additionally, individual blocks may be deleted from the method without departing from the spirit and scope of the subject matter described herein. Furthermore, the method can be implemented in any suitable hardware, software, firmware, or combination thereof. However, for ease of explanation, in the embodiments described below, the method may be considered to be implemented in the above-described system 102.

At block 1102, consents of patients undergoing a clinical trial may be obtained and consent data of the patients may be stored. The clinical trial may comprise a study setup stage, a study conduct stage, and a study closeout stage, wherein the study setup stage may be understood as an initial stage wherein necessary arrangements are being made for performing the clinical trial, the study conduct stage may be understood as a stage wherein the clinical trial is conducted, and the study closeout stage may be understood as a stage when the clinical trial is concluded.

At block 1104, consent data of the patients may be validated before progressing onto the study setup stage, the study conduct stage, and the study closeout stage of the clinical trial. In case, consent data of a patient is not found to be available, a prompt may be provided to the patient for providing his consent.

At block 1106, data associated with a clinical trial site for performing the clinical trial may be collected. The data associated with the clinical trial site may include details associated with the clinical trial site, number of patients registering at the clinical trial site to undergo the clinical trial, a record of patients undergoing a single blinded study, a record of patients undergoing a double blinded study, a record of patients dropping out of the clinical trial, the clinical data of the patients, and the non-clinical data of the patients throughout the clinical trial and any other data related to the patients registered at the clinical trial site.

At block 1108, the patients may be randomly grouped into two or more groups for performing one or more of a single blinded study and a double blinded study during the clinical trial. The patients may be grouped into the two or more groups based on the clinical data and the non-clinical data of the patients. A unique QR code may be assigned to each of the patients for allowing the patients to track and complete activities associated with one or more of the single blinded study and the double blinded study.

At block 1110, clinical data and non-clinical data of the patients may be collected. The clinical data may include medical details of the patients collected before and after administration of a drug during the clinical trial, and the non-clinical data may include personal details and documents of the patients collected for performing patient registration and administration for the clinical trial.

At block 1112, one or more of timelines, progress, compliance, and data associated with different stages of the clinical trial may be managed.

Although implementations for methods and systems for managing a clinical trial of patients have been described in language specific to structural features and/or methods, it is to be understood that the appended claims are not necessarily limited to the specific features or methods described. Rather, the specific features and methods are disclosed as examples of implementations for classifying components of a product.

Exemplary embodiments discussed above may provide certain advantages. Though not required to practice aspects of the disclosure, these advantages may include those provided by the following features.

Some embodiments of the system and the method may reduce time and efforts involved in acquiring and interpreting data at individual stages of the clinical trial by providing a unified platform.

Some embodiments of the system and method facilitate real time analysis of the clinical data and the non-clinical data obtained during the clinical trial.

Some embodiments of the system and method provide fully automated decision making and insights to the sponsors of clinical trials about the progress of the clinical trial.

Some embodiments of the system and method ensure error free collection, analysis, and audit of the data associated with the clinical trial site, the clinical data, and the non-clinical data of the patients.

We claim:

1. A system for managing a clinical trial of patients, the system comprising:
   a memory; and
   a processor coupled to the memory, wherein the processor is configured to execute a set of one or more instructions stored in the memory to:
      obtain consent data a patient registered for the clinical trial, wherein the patient is associated with a clinical trial site;
      authenticate the consent data by receiving a unique authentication code from a device associated with the patient;
      obtain patient data comprising clinical data and non-clinical data, wherein the patient data is obtained by:
      determining offline status:
      assign a timestamp and a geographical location, while offline, to the patient data;
      configure the device to encrypt the patient data using a data encryption scheme;
      store the encrypted patient data;
      detect connectivity of the device to internet to synchronize the encrypted data; and
      synchronize the encrypted patient data upon detection of the internet connectivity;
      transmit notification automatically to the patient and the clinical trial site for recording the patient data based on timelines in a compliance calendar for the patient, wherein the compliance calendar comprises date, time, and a type of clinical data type and non-clinical data corresponding to a stage of the clinical trial;
      randomly group patient based on the clinical data and the non-clinical data for performing blinded study in the clinical trial using one of a permuted blocked stratification and a minimization technique for randomly grouping the patient;
      assign a unique Quick Response (QR) code to the patient in the group for tracking completeness of activities assigned to the patient during the clinical trial, wherein the activities are assigned based on the obtained patient data;
   automatically manage one or more of timelines, progress, compliance, and data associated with the stage of the clinical trial, based on the compliance calendar; and
   generate in real time an analysis report indicating a change in a level of one or more parameters associated with the clinical trial site, the clinical data, and the non-clinical data of the patient over a period of time of the clinical trial for performing the blinded study, wherein the one or more parameters include one or more symptoms, compliance, and number of patients dropping out.

2. The system of claim 1, the processor is further configured to provide another analysis report of the data associated with the clinical trial site, the clinical data, and the non-clinical data of the patient in real time.

3. The system of claim 1, wherein the processor is further configured to map one or more adverse events reported by the patient and one or more adverse events identified at the clinical trial site.

4. The system of claim 1, wherein the system is connected with the device including an offline data recorder capable of recording the clinical data and the non-clinical data when the device lacks internet access.

5. The system of claim 4, wherein the device includes a communication unit for synchronizing the clinical data and the non-clinical data to the system when the device has internet access.

6. The system of claim 1, wherein a randomizer assigns the unique QR code to patient for allowing tracking and completeness of activities associated with the blinded study, wherein the blinded study comprises a single blinded study and a double blinded study.

7. The system of claim 1, further comprises a clinical trial auditor configured to provide an audit trial report and allowing a real time inspection of studies performed during the clinical trial, wherein the audit trial report includes details of a person entering, capturing, and modifying data, and time at which the data is entered, captured and modified during the clinical trial.

8. The system of claim 7, wherein the clinical trial auditor is integrated with a clinical site data collector for automatically fetching details of a new clinical trial site defined in the clinical site data collector.

9. The system of claim 1, wherein the processor is configured to provide access to one or more of:
   compliance data of the clinical trial site;
   consent data of the patient tagged with a time stamp and a geographic location; and
   Patient Health Information (PHI), wherein a partial access or a complete access of the PHI is provided to a user based on access rights defined for the user.

10. The system of claim 6, wherein the randomizer randomly groups the patient by obtaining details from a clinical site data collector for performing the single blinded study and the double blinded study.

11. The system of claim 1, further comprises an automatic medical coder to generate a mapping of medical terms with standard dictionary terms.

12. The system of claim 1, wherein the processor is further configured to:

create the compliance calendar for the patient of the clinical trial.

13. The system of claim 1, wherein the processor is further configured to:

automatically retrieve digital information of the patient from one or more databases, wherein the one or more databases include Electronic Health Records (EHR), and wherein the digital information comprises data associated with the clinical trial site, treatment group, and date and time stamp of last update of the patient.

14. The system of claim 13, wherein the processor is further configured to store centrally the consent data, the patient data, and the retrieved digital information.

15. A system for managing a clinical trial of patients, the method comprising:

obtaining consent data a patient registered for the clinical trial, wherein the patient is associated with a clinical trial site;

authenticating the consent data by receiving a unique authentication code from a device associated with the patient;

obtaining patient data comprising clinical data and non-clinical data, wherein the patient data is obtained by:

determining offline status;

assigning a timestamp and a geographical location, while offline, to the patient data;

configuring the device to encrypt the patient data using a data encryption scheme;

storing the encrypted patient data;

detecting connectivity of the device to internet to synchronize the encrypted data; and synchronizing the encrypted patient data upon detection of the internet connectivity;

transmitting notification automatically to the patient and the clinical trial site for recording the patient data based on timelines in a compliance calendar for the patient, wherein the compliance calendar comprises date, time, and a type of clinical data type and non-clinical data corresponding to a stage of the clinical trial;

randomly group patient based on the clinical data and the non-clinical data for performing blinded study in the clinical trial using one of a permuted blocked stratification and a minimization technique for randomly grouping the patient;

assigning a unique Quick Response (QR) code to the patient in the group for tracking completeness of activities assigned to the patient during the clinical trial, wherein the activities are assigned based on the obtained patient data;

automatically manage one or more of timelines, progress, compliance, and data associated with the stage of the clinical trial, based on the compliance calendar; and generating in real time an analysis report indicating a change in a level of one or more parameters associated with the clinical trial site, the clinical data, and the non-clinical data of the patient over a period of time of the clinical trial for performing the blinded study, wherein the one or more parameters include one or more symptoms, compliance, and number of patients dropping out.

16. The method of claim 15, further comprises: providing a combined analysis of the data associated with the clinical trial site, the clinical data, and the non-clinical data of the patient in real time.

17. The method of claim 15, further comprises mapping one or more adverse events reported by the patient and one or more adverse events identified at the clinical trial site.

18. The method of claim 15, further comprises assigning the unique QR code to the patient, for allowing tracking and completeness of activities associated with the blinded study, wherein the blinded study comprises a single blinded study and a double blinded study.

19. The method of claim 15 further comprises:

creating the compliance calendar for the patient of the clinical trial.

\* \* \* \* \*